United States Patent [19]

Trainin

[11] 4,250,084
[45] Feb. 10, 1981

[54] PURIFIED THYMIC HORMONE (THF), ITS PREPARATION AND PHARMACEUTICAL COMPOSITIONS CONTAINING IT

[75] Inventor: Nathan Trainin, Rehovot, Israel

[73] Assignee: Yeda Research and Development Company Limited, Rehovot, Israel

[21] Appl. No.: 942,722

[22] Filed: Sep. 18, 1978

Related U.S. Application Data

[63] Continuation of Ser. No. 700,238, Jun. 28, 1976, abandoned.

[30] Foreign Application Priority Data

Jul. 4, 1975 [IL] Israel .................................. 47645

[51] Int. Cl.³ ........................ C07G 7/00; A61K 37/02
[52] U.S. Cl. ................................. 260/112 R; 424/95; 424/177
[58] Field of Search ..................... 260/112 R; 424/95

[56] References Cited

U.S. PATENT DOCUMENTS

| | | | |
|---|---|---|---|
| 3,438,859 | 4/1969 | De Somer et al. | 424/95 X |
| 3,466,367 | 9/1969 | Jaeger et al. | 424/95 |
| 3,657,417 | 4/1972 | Brunetti et al. | 424/95 |
| 4,010,148 | 3/1977 | Goldstein | 260/112 R |
| 4,077,949 | 3/1978 | Goldstein | 260/112.5 R |

OTHER PUBLICATIONS

Souadjian et al., *Chemical Abstracts*, vol. 75:32,928y (1971).
Comsa et al., *Chemical Abstracts*, vol. 53:2335a (1959).
Carnaud et al., *J. Expl. Med.*, vol. 138 (1973), pp. 1521-1532.
Kook et al., *Cellular Immunology*, vol. 19, (1975), 151-157.
Trainin et al., *J. Expl. Med.*, vol. 132, No. 5 (1970), 885-897.

*Primary Examiner*—Walter C. Danison
*Attorney, Agent, or Firm*—Ladas & Parry

[57] ABSTRACT

Chemically substantially pure and uniform THF (thymic hormone), substantially devoid of endotoxins, having a molecular weight of 3323±220, an isoelectric point of from 5.7 to 5.9; an amino acid composition of approximately: aspartic acid—4 units; threonine—1 unit; serine—5 units; glutamic acid—8 units; proline—2 units; glycine—5 units; alanine—2 units; leucine—1 unit; lysine—1 unit; arginine—2 units; ½ cystine—1 to 2 units; being the product of purification of thymus tissue and removal there from of endotoxins, and a process for the preparation of same which comprises:

(a) comminuting fresh thymus tissue from mammals in a suitable liquid medium; at a pH between 7 and 8;
(b) removing cell debris and other cell residues by centrifugation and ultracentrifugation;
(c) separating the supernatant liquid and filtering same through suitable filtration media to remove particulate material and so as to sterilize the passing liquid and to remove endotoxins,
(d) subjecting the liquid to exhaustive dialysis;
(e) lyophilizing the dialyzate and redissolving it in a suitable liquid medium;
(f) subjecting the lyophilized redissolved material to gel filtration and assaying the resulting peaks (fractions), and
(g) eluting the active constituent in substantially pure form; and pharmaceutical compositions of matter containing same as active ingredient and a process of immunorestorative therapy of mammals which comprises administering to the mammal a therapeutically effective dose of such THF.

9 Claims, 2 Drawing Figures

PURIFIED THYMIC HORMONE (THF), ITS PREPARATION AND PHARMACEUTICAL COMPOSITIONS CONTAINING IT

This is a continuation of application Ser. No. 700,238 filed June 28, 1976 now abandoned.

BACKGROUND OF THE INVENTION

The present invention relates to a process for the preparation of a chemically substantially pure thymic hormone, designated as THF, to the purified substance as novel composition of matter, to pharmaceutical preparations containing said purified thymic hormone THF as active ingredient and to processes of immunosupportive therapy and to other methods of treatment making use of said novel purified composition of matter.

It is known for some time that the impaired capacity of neonatally thymectomized (NTx) animals to reject skin grafts and to induce graft-versus-host (GVH) response are partially restored either by implantation of cell-impermeable diffusion chambers containing thymus tissue, or by injection of cell-free thymic extracts. It has been shown that extracts containing the thymic hormone increase the cytotoxic reactivity of lymphoid cells against syngeneic tumors in vitro and in vivo, see Trainin et al, J. Exp. Med., 138: 1521 (1973).

In view of the recognition of the important and valuable characteristics of the thymic hormone THF, it was considered to be of considerable advantage and value to try and obtain this in a chemically purified form, so as to make it possible to use it in medicine, as well as in research without the complications and drawbacks of preparations wherein such hormone is combined with various other constituents, such as proteins, hormones, etc. Only a purified substance can be used with a minimum of side-effects, and only a purified substance can be standardized so as to make possible an accurate dosage of such substance in medical applications.

SUMMARY OF THE INVENTION

According to the present invention there is provided a novel process for the preparation of substantially pure THF starting with thymus tissue from any suitable source. Although herein the preparation of purified THF is illustrated with reference to fresh calf thymus as source, it is to be understood that this is by way of example only and that other similar sources of thymus hormone can be used.

The process according to the present invention comprises essentially homogenizing fresh thymus in a suitable volume of a liquid medium, such as buffer, saline or the like, removing the cell debris; removing further undesired constituents by ultra-centrifugation, filtering the remaining liquid through suitable membrane filters and subjecting the thus obtained sterile fluid to exhaustive dialysis, liophilizing the dialyzate, redissolving same and fractionating same (by gel filtration or any other suitable technique), evaluating the individual protein fractions (protein peaks) for its biological activity, eluting the active material, and subjecting same to further fractionation (such as by ion exchange chromatography) until substantially pure and biologically active THF is obtained; which is characterized thereby that it constitutes a single defined band of protein upon analysis by electrophoretic focusing, and it is devoid of pyrogenous constituents (endotoxins).

The resulting pure THF is a polypeptide; it has a molecular weight of about 3323 ($\pm$220), an isoelectric point between 5.5 and 6.0, and it is believed to comprise 32 ($\pm$2) amino acids as follows:

TABLE 1

Analysis of amino acid composition of THF[a]

| Amino acid residue | nmoles | No. of residues (leucine = 1) |
|---|---|---|
| Asx | 160.98 | 4 |
| Thr | 45.02 | 1 |
| Ser | 186.07 | 5 |
| Glx | 280.20 | 8 |
| Pro | 72.50 | 2 |
| Gly | 170.60 | 5 |
| Ala | 66.30 | 2 |
| Leu | 36.44 | 1 |
| Lys | 49.64 | 1 |
| Arg | 57.65 | 2 |
| ½ Cyst | 60.00 | 1-2 |
| | Sum | 32 $\pm$ 2 |

[a]The amino acid analysis (320 μg protein of THF) shows no unusual amino acids. Based on leucine as unit, the minimal molecular weight is 3323 $\pm$ 220.

More specifically, the preparation of purified THF comprises according to a preferred embodiment the following steps:

(1) Homogenizing fresh calf thymus in 1–5 volumes of sodium phosphate buffer, PBS, saline, Tris-buffer, etc., pH ranging between 7 to 8. This step is performed with wet weight of thymus material ranging between 150 gr to 1,000 gr and adequate proportions of buffer solutions;

(2) centrifuging the homogenate in the cold at a low speed to remove cell debris;

(3) subjecting the supernatant to ultracentrifugation. The time and speed centrifugation varies according to the amount of material in preparation. The g velocity ranges between 90,000 to 150,000 g and the time of centrifugation between 2 to 5 hours;

(4) discarding the precipitate, filtering the supernatant through various membrane filters ranging from 0.8 to 0.45 μm for removal of particulate materials and sterilization; removing also pyrogenous components, endotoxins;

(5) submitting the sterile supernatant to exhaustive dialysis against larger volumes of distilled water, saline, PBS, etc. for 24 to 60 hours in the cold. Cellophane dialysis bags adequate for filtration of materials less than 10,000 molecular weight are used. The active material passes through the dialysis bags during this procedure;

(6) lyophilizing the dialyzate and redissolving it in distilled water, in ammonium bicarbonate, in PBS, in Tris-buffer, etc., and diluting to protein concentrations ranging from 1 to 5 mg/ml of solvent. This lyophilizate contains the active principle of THF;

(7) fractionating the lyophilized redissolved preparation by gel filtration on Sephadex columns ranging from G10 to G50. Other bio gel columns can be interchanged with Sephadex. Each of the protein peaks obtained is lyophilized, redissolved in water, ammonium bicarbonate or Tris-buffer and checked for activity in the assays specified above to determine its biological activity;

(8) fractionating the active material-eluted from the columns by ion exchange chromatography. The column is eluted with Tris-buffer, ammonium bicarbonate, etc., preferably with a linear concentration gradient of salt. The peak eluted in a constant concentration of salt (0.12 to 0.15 M) is pure and contains substantially all the entire active THF of the starting material;

(9) if desired, the active material is further filtered through Sephadex or similar columns to remove salts without interfering with its activity. The degree of purity of THF was analyzed by electrophoretic focusing on polyacrylamide gels of pH gradient from 3.5 to 10. This reveals the presence of only one band of protein. The isoelectric point obtained for this protein band ranges between 5.5 and 6.0.

The bioassays used to evaluate the biological activity of THF are as follows:

(1) The effect of THF in the in vitro graft versus host model (Auerbach, R., and Globerson, A., Exp. Cell. Res. 42: 31, 1966; Trainin, N., Small, M., and Globerson, A., J. Exp. Med. 130: 765, 1969 and Trainin, N., and Small, M., J. Exp. Med. 132: 885, 1970).

(2) The effect of THF in intracellular cAMP and on membranal adenyl cyclase activity (Kook, A. I., and Trainin, N., J. Exp. Med. 139: 193, 1974; Kook, A. I., and Trainin, N., J. Immunol. 114: 157, 1975 and Trainin, N., Kook, A. I., Umiel, T. and Albala, M., Ann. N.Y. Acad. Sci. 249, 349, 1975).

(3) The effect of THF in mixed lymphocyte culture (MLC) (Umiel, T., and Trainin, N., Eur. J. Immunol. 5: 85, 1975 and Trainin, N., Kook, A. I., Umiel, T. and Albala, M., Ann. N.Y. Acad. Sci. 249: 349, 1975).

(4) The effect of THF in the mitogenic activity of PHA and Concanavalin A (Rotter, V., and Trainin, N., Cell. Immunol. 16: 413, 1975).

(5) The effect of THF on the killing capacity of T-lymphocytes against tumor cells (Carnaud, C., Ilfeld, D., Brook, I., and Trainin, N., J. Exp. Med. 138: 1521, 1973 and Small, M., and Trainin, N., Int. J. Cancer, 15, 962 (1975).

(6) The effect of THF in a proliferative capacity of bone marrow stem cells (Zipori, D., and Trainin, N., Exp. Haemat., 3, 389-398 (1975)

(7) The effect of THF against autosensitization (Trainin, N., Small, M., Zipori, D., Umiel, T., Kook, A. I., and Rotter, V., in "Biological activity of thymic hormones" (D. W. van Bekkum and A. M. Kruisbeek, eds.), 1975.

DESCRIPTION OF THE PREFERRED EMBODIMENT

The following example serves to illustrate the process of the present invention. It is clear that this example is by way of illustration only and that various changes and modifications in the process steps can be resorted to without departing from the scope and spirit of the present invention.

EXAMPLE

The purified THF was prepared by starting with fresh calf thymuses. These were homogenized in two volumes of 0.005 M sodium phosphate buffer pH 7.4 and centrifuged at 2500 g for 20 min. The process was started with three calf thymuses (400–500 g total wet wt) and following homogenization and removal of cell debris a total amount of 4200 mg protein was obtained for further processing. The supernatant was further centrifuged at 105.000 g for 5 hours and diluted to a standard protein concentration. This active extract was then exhaustively dialyzed against a 20 times larger volume of distilled water for 60 hours in the cold. The THF passes through Union Carbide dialysis sacs no. 27/32 or 23/32 while the portion retained in the dialysis sacs is devoid of activity, suggesting that the molecular weight (MW) of the active agent is roughly 6000 or less.

Figure 1:
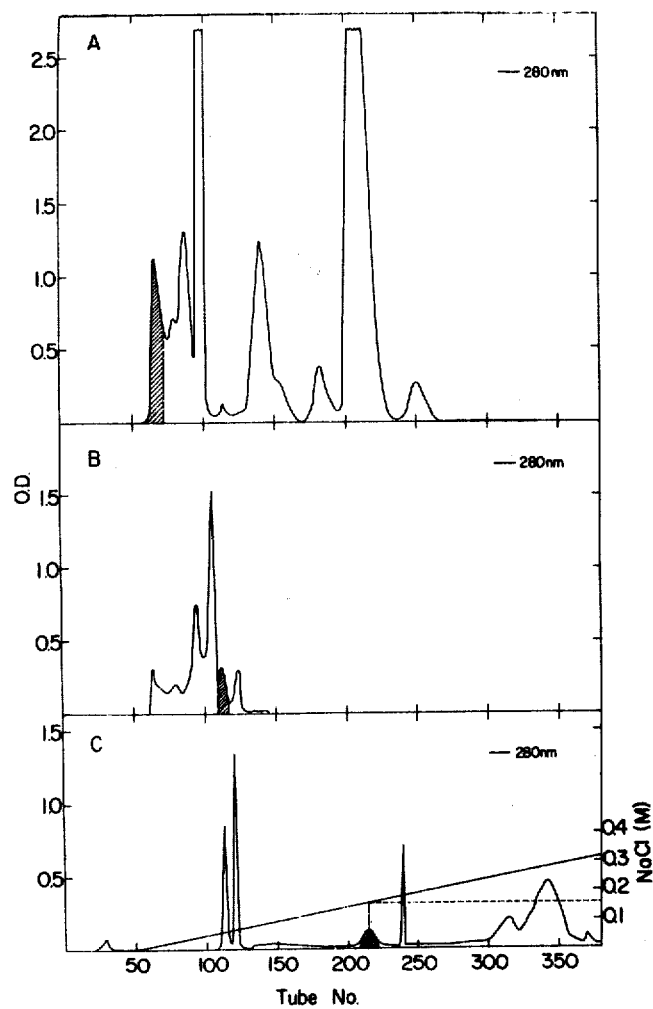
Figure 2:
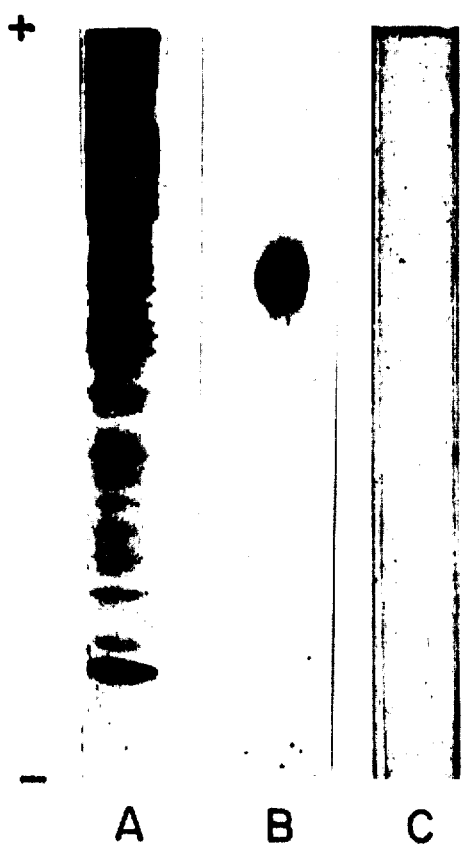

Protein, RNA, DNA, and reducing carbohydrates contents of the dialyzate which has been concentrated by lyophylization were determined. No DNA could be detected. However, a constant ratio of about 7 mg protein to 2 mg reducing carbohydrates and 1 mg RNA was obtained. This lyophylized dialyzate was treated with both DNase and RNase and these enzymes did not abolish the activity of the preparation. In contrast, the preparation was inactivated by pronase. This partially purified preparation of THF was stable when kept at $-20°$ C. for several months, but lost activity after 48 hours at room temperature. The lyophilized preparation was then dissolved in 0.1 M ammonium bicarbonate pH 8.0 and fractionated by gel filtration on Sephadex G-10 column (Pharmacia) (FIG. 1A). Each of the protein peaks obtained was lyophilized, redissolved in ammonium bicarbonate, and checked for activity. It was found that only substances which were eluted in the void volume of the column possess the ability to induce spleen cells from NTx mice to react in the in vitro GVH assay (FIG. 1A and Table 2). The molecular weight of THF thus appears to be greater than 700 since substances with a molecular weight above 700 are eluted in the void volume of G-10 Sephadex columns.

The material eluted with the void volume of the G-10 column was further fractionated by gel filtration on Sephadex G-25 fine column (Pharmacia) (FIG. 1B). The column was eluted with 0.1 M ammonium bicarbonate pH 8.0. The resulting peaks were again lyophilized, redissolved, and checked for their activity in the in vitro GVH assay system. Activity was consistently found in one peak only (FIG. 1B and Table 2). The G-25 Sephadex column was calibrated with insulin (Sigma) (MW 5700), glucagon (Eli Lilly) (MW 3460), and bacitracin (Teva, Israel) (MW 1400). The elution volume of these substances was found to be inversely proportional to their molecular weights. The active material of the thymus extract (THF) was eluted immediately after glucagon. It thus appears that molecular weight of THF is about 3000. The components of the active peak eluted from the G-25 Sephadex column were further fractionated by anion exchange chromatography on DEAE-Sephadex A-25 (Pharmacia) in 0.1 M Tris-HCl pH 8.0. The column was developed with a linear concentration gradient of NaCl (FIG. 1C). Similar elution pattern can be obtained when the Tris-HCl buffer is replaced by 0.1 M NH$_4$HCO$_3$ pH 8.0. When the peaks obtained from the anion exchange column were tested, it was found that the peak eluted in 0.15 M NaCl contained all the activity (FIG. 1C and Table 2). This material was filtered through a G-10 Sephadex column to remove salts and the activity was recovered in the void volume of the column. Using columns of the above dimensions 10–20 microgram of active pure protein were obtained following this step. The material was concentrated by lyophilization, and its degree of purity was analyzed by isoelectric focusing on polyacrylamide gels. Eighty micrograms of protein were applied to the gels. The gels were subsequently stained either for proteins with Coomassie brilliant blue or for glycoproteins with Alcian blue. The active peak obtained from the anion exchange chromatography column revealed the presence of one band only which stained for protein while no glycopeptides were detected. The isoelectric point obtained for this polypeptide in three different runs ranged between 5.65–5.90. In parallel polyacrylamide gels which were not fixed and stained following the run were sliced, and the contents allowed to diffuse into water in the cold. Biological activity was recovered in the section corresponding to the protein band. This eluted material produced full activity in the vitro GVH assay at protein concentrations calculated to be below 1 μg and, therefore, could not be detected by the Lowry procedure. Thus it appears that the active peak eluted from the anion exchange chromatography column contains THF which is an acidic polypeptide having a molecular weight of about 3000. This is further confirmed by the analysis of the amino acid composition of THF (Table 1). This analysis was done using Beckman model 121 automatic amino acid analyzer. A sample of the active material was hydrolyzed in vacuum in 2 ml of 6 N hydrochloric acid at 110° C. for 22, 48, and 72 hours. The hydrolyzate was evaporated in a rotating evaporator at 50° C. The residue was dissolved in 0.2 N citrate buffer pH 2.2 and applied to the automatic column. Extrapolated back to zero time the number of residues for serine and threonine were 5.36 and 1.29, respectively, and accordingly were estimated as 5 and 1 (Table 1). A separate basic hydrolysis for tryptophan determination was not conducted. However, indirect evidence that this amino acid is not present is available. Indeed, the active material eluted from the final G-10 Sephadex column, lyophilized and redissolved to a concentration of 1.25 mg protein/ml exhibited an OD ratio at 230 nm/280 nm of 9.77, the OD at 280 nm being 0.09. Assuming an approximate MW of 3300, the concentration of the active polypeptide is, therefore, 0.4 mM. Since the molar absorptivity of tryptophan is 5600, and since only traces of tyrosine and no phenylalanine were detected, a 0.4 mM solution of tryptophan should have produced an OD of 2.24 at 280 nm. This calculation indicates that no tryptophan is present in the amino acid composition of the active polypeptide. Based on leucine as unit, the molecular weight is thus estimated at 3323. A high proportion of acidic amino acids can be observed.

The purified THF obtained according to the present invention can be effectively applied in human and veterinary medicine. THF is the hormone which induces maturation of incompetent T-cells into competent ones. Therefore THF increases the immunological response against a series of antigens, including certain types of malignant cells, and may be of benefit in some neoplastic diseases. Thus, it is an effective agent in immunosupportive therapy. Moreover, this physiological effect of THF can be used in the course of treatment of patients in which T-cell deficiency has been found. These include certain immunodeficiencies of children, such as thymic hypoplasia, Di George syndrome, Wiskott-Aldrich syndrome, and ataxia telangiectasia, and mongolism.

The purified THF, according to the present invention, is of special value in the treatment of severe viral disease accompanied by depression in cell-mediated immunity. The depression of cell-mediated immunity (CMI) can appear in the sequence of viral infections, resulting in a very fulminant course of the disease. Since competent cell-mediated immune responsiveness is essential for recovery from infections of this type, improvement in CMI, following THF administration, may have beneficial influence in the course of the disease. The application of THF is also of considerable value in patients with CMI depression following radiation or following cytotoxic treatment. This applies especially to patients with malignant diseases. THF-induced restoration of CMI enhances the resistance to infections of patients with malignancies and mades possible a more aggressive chemotherapy and radiation therapy.

Application of therapeutically effective dosages of THF is also of value in the treatment of diseases comprising autoimmune processes such as lupus erythematosus, rheumatoid arthritis, Hashimoto thyroiditis, chronic aggressive hepatitis.

Pharmaceutical compositions containing THF in purified form as active ingredient were administered to a number of patients.

A boy 3½ years old, with disseminated adenovirus infection and depressed CMI was in an apparently hopeless condition, comatose and with depression of the respiratory center. THF was administered by injection. The quantity used was about 20 mg of the purified THF per day. A dramatic clinical improvement, paralleled by restoration of normal CMI levels took place.

Two patients with acute lymphatic leukemia contracted varicella. The course is usually fulminant with high mortality. Upon administration of THF a relatively benign course of the disease took place.

A 2 year old girl with acute lymphatic leukemia contracted very severe pneumonia with CMI depression. Purified THF was administered at a dose of 0.75 mg/kg/day. After a few days a dramatic improvement was observed in her condition.

In two children, aged 10 and 11 years respectively, with subacute sclerosing panencephalities (SSPE) impairment of CMI was demonstrated by low T-cell number, decreased cAMP levels of peripheral blood lymphocytes and other criteria. Purified THF was administered during 10 days and 21 days respectively, the dose being 0.75 mg/kg/day. Results obtained showed that THF administration results in a reconstitution of impaired T-cell function in both patients.

The present invention also relates to pharmaceutical compositions of matter containing purified THF as active ingredient. The term "purified THF" refers to purified THF obtained by the process according to the present invention or by any other route or manner and which corresponds in its composition to that obtained according to the present invention.

Pharmaceutical compositions of matter, according to the present invention, contain from about 0.25 mg to 2.0 mg of purified THF per kg body weight of the mammal to which this is administered, in unit dosage form. For humans this corresponds to doses of about 5 mg to 100 mg per day of the purified substance. Calculated on the pure polypeptide, this means a dosage of from about 2 micrograms to about 20 micrograms pure THF per kg bodyweight per day. It is intended to encompass within the dosage envisaged by the present invention doses of from 1 microgram/kg/day to about 100/microgram/kg/day of pure THF.

Preferred pharmaceutical compositions are in the form of sterile injections, containing THF in a suitable carrier or diluent. The preferred mode of administration is by IM-injections. According to the present invention purified THF is obtained which is substantially free of pyrogenous components, and this avoids undesired side effects.

The purified THF can be used in conjunction with other drugs, such as for example with antibiotics, with bytotoxic drugs, and the like.

Tests were carried out with various types of mammals, and these have shown that compositions according to the present invention have a high efficacy in the treatment of conditions where a deficiency of T-cell function was present. Treatment brought about a restoration of T-cell count to normal. Animal experiments have shown that the application of compositions, according to the present invention, results in a substantial reduction of the rate of growth and incidence of various types of malignancies.

TABLE 2

The induction of in vitro GVH response in spleen cells of NTx C57BL/6 mice by active fractions obtained during various steps of the procedure for the isolation of THF

| Fraction tested (20 μg protein/ml) | Source of spleen cells | Incidence of reactive cultures | | | Culture response (%) |
| --- | --- | --- | --- | --- | --- |
| — | NTx | 0/5 | 0/5 | 1/5 | 7 |
| — | Intact | 4/5 | 4/5 | 5/5 | 87 |
| Dialyzate of thymus extract | NTx | 3/5 | 3/5 | 3/5 | 60 |
| Active peak of Sephadex G-10 column | NTx | 5/5 | 4/5 | 4/5 | 87 |
| Active peak of Sephadex G-25 column | NTx | 5/5 | 5/5 | 4/5 | 93 |
| Active peak of DEAE Sephadex A-25 column | NTx | 4/5 | 4/5 | | 80 |

I claim:

1. A THF active composition having a molecular weight of 3323±220; an isoelectric point of from 5.7 to 5.9; an amino acid composition of approximately: aspartic acid—4 units; threonine—1 unit; serine—5 units; glutamic acid—8 units; proline—2 units; glycine—5 units; alanine—2 units; leucine—1 unit; lysine—1 unit; arginine—2 units; ½ cystine—1 to 2 units; being the product obtainable by purification of thymus tissue and removal therefrom of endotoxins.

2. A process for preparing substantially pure and endotoxin-free THF which comprises:
   (a) comminuting fresh thymus tissue from mammals in a suitable liquid medium; at a pH between 7 and 8;
   (b) removing cell debris and other cell residues by centrifugation and ultracentrifugation;
   (c) separating the supernatant liquid and filtering same through suitable filtration media to remove particulate material and so as to sterilize the passing liquid and to remove endotoxins,
   (d) subjecting the liquid to exhaustive dialysis;
   (e) lyophilizing the dialyzate and redissolving it in a suitable liquid medium;
   (f) subjecting the lyophilized redissolved material to gel filtration and assaying the resulting peaks (fractions), and
   (g) eluting the active constitutent in substantially pure form.

3. A process according to claim 2, wherein the thymus is comminuted in 1 to 5 volumes of phosphate buffer, in saline, tris-buffer or the like, at a pH of from pH 7 to pH 8.

4. A process according to claim 2, wherein after ultracentrifugation, the remaining liquid is filtered through membrane filters of from 0.8 to about 0.45 μm.

5. A process according to claim 2, wherein the liquid obtained after removal of particulate matter is subjected to exhaustive dialysis against larger volumes of water, saline, PBS or the like.

6. A process according to claim 2, wherein the lyophilized dialysate is redissolved in distilled water, in ammonium bicarbonate, PBS, tris-buffer or the like so as to obtain a protein concentration of about 1 to 5 mg/ml of solvent.

7. A process according to claim 2, wherein the gel filtration is effected on Sephadex columns ranging from G-10 to G-50.

8. A process according to claim 2, wherein the fractions eluted by ion exchange chromatography are obtained from peaks substantially as defined by FIG. 1A.

9. A THF active composition obtainable by extraction from thymus cells by collection of the component eluted at 0.15 M NaCl from an anion exchange chromatograph on DEAE Sephadex A-25 equilibrated with 0.1 M Tris-HCl at pH 8.0.

* * * * *